(12) United States Patent
Kubota et al.

(10) Patent No.: US 7,309,710 B2
(45) Date of Patent: Dec. 18, 2007

(54) CRYSTALS

(75) Inventors: Hirokazu Kubota, Tsukuba (JP); Kiyoshi Iwaoka, Takahagi (JP); Sou Yamaguchi, Tsukuba (JP); Masaki Yokota, Tsukuba (JP)

(73) Assignee: Astellas Pharma Inc., Tokyo (JP)

( * ) Notice: Subject to any disclaimer, the term of this patent is extended or adjusted under 35 U.S.C. 154(b) by 177 days.

(21) Appl. No.: 10/525,709

(22) PCT Filed: Aug. 26, 2003

(86) PCT No.: PCT/JP03/10769

§ 371 (c)(1),
(2), (4) Date: Feb. 24, 2005

(87) PCT Pub. No.: WO2004/020433

PCT Pub. Date: Mar. 11, 2004

(65) Prior Publication Data

US 2006/0069130 A1    Mar. 30, 2006

(30) Foreign Application Priority Data

Aug. 27, 2002 (JP) .............................. 2002-246341

(51) Int. Cl.
*A61K 31/4439* (2006.01)
*C07D 401/12* (2006.01)

(52) U.S. Cl. .................................... 514/341; 546/275.4

(58) Field of Classification Search ............. 546/275.4; 514/341
See application file for complete search history.

(56) References Cited

U.S. PATENT DOCUMENTS

| 6,506,747 | B1 | 1/2003 | Betageri et al. | |
| 6,958,339 | B2 * | 10/2005 | Kubota et al. ......... | 514/255.05 |
| 2001/0011090 | A1 | 8/2001 | Kubota et al. | |

FOREIGN PATENT DOCUMENTS

| EP | 1024138 A1 | 8/2000 |
| JP | 2000-254358 A | 9/2000 |
| WO | WO99/19303 A1 | 4/1999 |
| WO | WO99/51580 A1 | 10/1999 |
| WO | WO99/62885 A1 | 12/1999 |

OTHER PUBLICATIONS

Halebian et al., "Pharmaceutical Applications of Polymorphism", Journal of Pharmaceutical Sciences, 58 (8), 1969, pp. 911-929.*
Chemical & Engineering News, Feb. 2003, pp. 32-35.*
Brittain et al., "Polymorphism in Pharmaceutical Solids" NY: Marcel Dekker, Inc., 1999, pp. 1-2, 185.*
U.S. Pharmacopis #23, National Forumulary #18 (1995) pp. 1843-1844.*
Muzaffar et al., "Poylmorphism and Drug Availability", J of Pharmacy (Lahore) (1979), 1(1), pp. 59-66.*
Jain et al., "Polymorphism in Pharmacy" Indian Drugs, 1986, 23(6), pp. 315-329.*
Taday et al., "Using Terahertz Pulse, etc.," J of Pharmaceutical Sciences, 92(4), 2003, pp. 831-838.*
Concise Enclyclopedia Chemistry, VY: Walter de Bruyter Berlin, 1993, pp. 872-873.*
Wall et al., "Pharmaceutical Applications, etc.," Pharmaceutical Manufacturing, 3(2), 1986, pp. 32-34.*
Otsuka et al., "Effect of Polymorphis Forms, etc.," Chem. Pharm. Bull. 47(6), 1999, pp. 852-856.*
Doelker et al. C 138 :209993, 2002.*
Ulicky et al., "Comprehensive Dictionary of Physical Chemistry", NY:PTR Prenctice Hall 1992, p. 21.*
Japan Patent Office, machine-generated translation of JP 2000-256358, Sep. 19, 2000.
Patent Abstracts of Japan, JP 2000-256358, Sep. 19, 2000.

* cited by examiner

*Primary Examiner*—Patricia L. Morris
(74) *Attorney, Agent, or Firm*—Sughrue Mion Pllc.

(57) ABSTRACT

Obtaining the crystal of 4,6-dimethyl-4'-[3,5-bis(trifluoromethyl)-1H-pyrazol-1-yl]nicotinanilide having excellent activity of inhibiting $Ca^{2+}$ release-activated $Ca^{2+}$ channel and suppressing IL-2 production to find that the compound includes the presence of two types of polymorphic crystals and that any of the crystals is preferable as a raw material for producing pharmaceutical compositions.

6 Claims, 4 Drawing Sheets

US 7,309,710 B2

CRYSTALS

TECHNICAL FIELD

The present invention relates to a novel crystal of 4,6-dimethyl-4'-[3,5-bis (trifluoromethyl)-1H-pyrazol-1-yl]nicotinanilide useful as an inhibitor of $Ca^{2+}$ release-activated $Ca^{2+}$ channel.

BACKGROUND OF THE INVENTION

It is known that $Ca^{2+}$ release-activated $Ca^{2+}$ channel (abbreviated as CRACC hereinafter; also called store-dependent $Ca^{2+}$ channel) exists in almost all inflammatory cells such as mast cells, lymphocytes and astrocytes (J. Biol. Chem., 270, p 29-32 (1995)). It is also reported that it is deeply involved in cytokine production, lipid mediator release, and the like (J. Immunol., 155, p 286-96 (1995) and Br. J. Pharmacol., 144, p 598-601 (1995)).

Additionally, it is known that CRACC exists also in endothelial cells (Am. J. Physiol., 269, C733-8 (1995)) and epithelial cells (J. Biol. Chem., 270, p 169-75 (1995)). It has been reported that sustained calcium influx is involved in the radical damage of endothelial cells (Am. J. Physiol., 261, C889-896 (1991)), suggesting that CRACC inhibitors have protective efficacy on endothelial cell-concerned tissue damages. Further, it has been reported that blockages of calcium influx inhibit cell proliferation and interleukin-2 (IL-2) production (Br. J. Pharmacol., 133, p 861-8 (1994)). CRACC inhibitors are useful as agents for preventing and treating proliferative or progressive diseases such as malignant tumors and autoimmune diseases and are also useful as suppressors for tissue rejection on transplantation.

Therefore, it is expected that CRACC inhibitors can be pharmaceutical agents useful for preventing or treating various inflammatory diseases, allergic diseases, autoimmune diseases, tissue damages, proliferative diseases, and the like.

A pyrazole derivative having a high inhibition selectivity for CRACC over voltage-operated $Ca^{2+}$ channel (abbreviated as VOCC hereinafter) involved in intracellular calcium regulation of excitatory cells such as smooth muscle cells and nerve cells and having an inhibitory activity against IL-2 production has been reported (for example, patent reference 1).

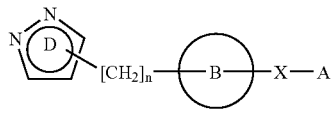

(In the formula, D represents pyrazolyl which may be substituted with halogeno-lower alkyl, or the like; n represents 0 or 1; B represents for example phenylene; X represents for example —$NR^1$—$CR^2R^3$—; A represents for example monocyclic or bicyclic or tricyclic fused heteroaryl which may have one or more substituents; see the official gazette about the detail.)

Additionally, other pyrazole derivatives having an inhibitory activity against IL-2 production and being useful as an agent for treating autoimmune diseases have also been reported (for example, patent references 2 and 3). The patent reference 2 discloses the following compound.

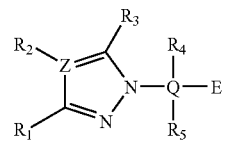

(In the formula, $R_1$ and $R_3$ represent for example perfluoroalkyl with 1 to 15 carbon atoms; Z represents nitrogen or carbon; Q represents for example aryl; and E represents for example -$L_3$-B; see the official gazette about the detail.)

The patent reference 3 discloses the following compound.

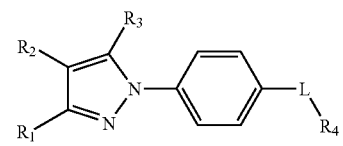

(In the formula, $R_1$ and $R_3$ represent for example $CF_3$; and L represents for example —NHC(O)—; see the official gazette about the detail.)

4,6-Dimethyl-4'-[3,5-bis (trifluoromethyl)-1H-pyrazol-1-yl]nicotinanilide may be included in the claims of patent references 1 to 3, but it is a novel compound which is not specifically disclosed therein.

Patent reference 1
Pamphlet of International Publication No. 99/19303
Patent reference 2
Pamphlet of International Publication No. 99/51580
Patent reference 3
Pamphlet of International Publication No. 99/62885

When a compound is to be used as a pharmaceutical product, generally, the compound is used preferably in the form of crystal from the standpoint of stability. For handling and constant quality, additionally, it is sometimes necessary to control the crystal polymorphism of the compound.

DISCLOSURE OF THE INVENTION

The present inventors made studies for the purpose of providing a novel pharmaceutical product selectively inhibiting CRACC and being useful for preventing and treating various inflammatory diseases and allergic diseases. As a result, the inventors obtained 4,6-dimethyl-4'-[3,5-bis (trifluoromethyl)-1H-pyrazol-1-yl]nicotinanilide as a crystal and found unexpectedly that the crystal of the compound includes two polymorphic types. Further, the inventors found that any of the polymorphic crystals was preferable as a raw material for producing pharmaceutical compositions.

Specifically, the invention relates to the polymorphic crystals of 4,6-dimethyl-4'-[3,5-bis(trifluoromethyl)-1H-pyrazol-1-yl]nicotinanilide useful as a raw material for producing pharmaceutical compositions.

The invention will be explained below in detail.

The invention relates to the crystal of 4,6-dimethyl-4'-[3,5-bis (trifluoromethyl)-1H-pyrazol-1-yl]nicotinanilide. The crystal of the invention may be stable enough to be used as a raw material for producing pharmaceutical products and is particularly preferably α type or β type crystal having the following physicochemical values. Each of the crystals is characterized by the following X-ray powder diffraction patterns [2θ(°)]. Herein, interplanar spacings and overall pattern are important for identification of crystal in the X-ray powder diffraction, due to the characteristic of the data. Because relative intensity changes more or less, depending on the crystal growth direction, particle size and measuring conditions, the relative intensity should not be understood strictly.

α type: 5.94, 9.94, 15.64, 15.88, 18.48, 20.04 and 20.76.
β type: 10.60, 12.90 and 17.24.

By the DSC analysis, the α type crystal has an endothermic peak at about 196° C. (onset: the temperature at which peak rises). The β type crystal has a very small peak around 172 to 174° C. based on phase transition and further has an endothermic peak at about 196° C. (onset). In other words, both the α type and β type crystals have endothermic peaks at 195° C. to 198° C. (onset).

Because both the α type and β type crystals are stable at 5 to 60° C. for at least three months and can be highly purified by recrystallization, these crystals may be used as raw materials for producing pharmaceutical products. Particularly, these crystals are preferable as raw materials for producing solid pharmaceutical preparations.

The results of a stability test, for example, at 40° C. under light-resistant are shown in Table 1.

TABLE 1

Stability test at 40° C. under light-resistant

|  | After 1 month | After 3 months |
|---|---|---|
| α type crystal | 100.7% | 99.2% |
| β type crystal | 99.7% | 100.7% |

(The values express the assay values determined by an internal standard method on the basis of peak area obtained by HPLC)

The α type crystal can be obtained by recrystallization in toluene. Additionally, the α type crystal may also be obtained by stirring a suspension of the β type crystal in a mixed solvent of 2-propanol and water at room temperature to under heating, preferably at 30 to 60° C., more preferably at 40 to 50° C. for several hours to several days. In other words, the α type crystal is a crystal form which is suitable for large-scale production in view of the stability in a suspension.

The β type crystal can be obtained by adding water (preferably, water of an equal volume to that of 2-propanol) to the 2-propanol solution with stirring. In other words, the β type crystal is excellent in that the crystal can be produced directly using a solvent with lower toxicity than that of toluene and the like.

For recrystallization of any of the α type and β type crystals, it is preferable to use the intended crystal separately obtained as a seed crystal.

By dissolving such crystal under heating, using a mixed solvent of 2-propanol and water (for example, at a mixing ratio of 4:3, respectively), and cooling the resulting solution with standing to allow the crystal to precipitate, a crystal having the same thermal absorption peak as the α type crystal in the DSC analysis and the same diffraction pattern as that of the α type crystal except for the peak at 2θ=19.24° in the X-ray powder diffraction may sometimes be obtained. The crystal is stable at room temperature. Based on the results of the DSC analysis and X-ray powder diffraction thereof, the crystal is also included in the α type crystal of the present invention.

Additionally, the present invention relates to a solid pharmaceutical composition comprising the crystal of 4,6-dimethyl-4'-[3,5-bis(trifluoromethyl)-1H-pyrazol-1-yl]nicotinanilide and a pharmaceutically acceptable carrier.

INDUSTRIAL APPLICABILITY 4,6-Diemthyl-4'-[3,5-bis(trifluoromethyl)-1H-pyrazol-1-yl]nicotinanilide is excellent in terms of the CRACC inhibitory activity, the inhibition selectivity over VOCC, and the activity of suppressing IL-2 production. Further, it exerted very good activities at tests described in the patent reference 1, including an effect on the suppression of TNCB-induced Contact Hypersensitivity, an activity of suppressing the arthritis in murine collagen-induced arthritis model, an activity of suppressing of antigen-induced airway eosinophilia (rat) and the like. Therefore, a pharmaceutical product containing the compound is useful as an agent for preventing or treating allergic, inflammatory or autoimmune diseases in which CRACC and IL-2 participates. Herein, the allergic, inflammatory or autoimmune diseases include, for example, bronchial asthma, psoriasis, atopic diseases including atopic dermatitis, inflammatory bowel diseases including Crohn disease, digestive ulcer, nephritis, hepatitis, pancreatitis, collagenosis, rheumatoid arthritis, osteoarthritis, and rejection on transplantation. The usefulness on these diseases can be confirmed at the in vitro tests of the CRACC inhibitory activity and the activity of suppressing IL-2 production as described in the patent reference 1 and at various tests using, for example, antigen-induced airway eosinophilia model as a typical disease model of bronchial asthma, and murine collagen-induced arthritis model. 4,6-Dimethyl-4'-[3,5-bis(trifluoromethyl)-1H-pyrazol-1-yl]nicotinanilide may be produced by the method described in the patent reference 1.

The solid pharmaceutical composition comprising the crystal of 4,6-dimethyl-4'-[3,5-bis(trifluoromethyl)-1H-pyrazol-1-yl]nicotinanilide as the active ingredient of the present invention may be prepared by methods for general use, using pharmaceutical carriers, excipients and the like for general use in the field. Dosing may be carried out by any dosage forms for oral administration in the forms of tablets, pills, capsules, granules, powders, liquids, and the like, or parenteral administration in the forms of injections into joints, veins, muscles, and the like, suppositories, transdermal liquids, ointments, transdermal attachments, transmucosal liquids, transmucosal plasters, inhalation agents, and the like. Particularly, tablets, pills, capsules, granules, powders, and the like for oral administration and inhalation agents, transnasal agents, and the like for parenteral administration using the crystal of 4,6-dimethyl-4'-[3,5-bis(trifluoromethyl)-1H-pyrazol-1-yl]nicotinanilide as a raw material for the production thereof are advantageous as stable solid formulations.

For a solid formulation for oral administration, the compound of the present invention is mixed with at least one inert excipient, such as lactose, mannitol, glucose, hydroxypropyl cellulose, microcrystalline cellulose, starch, polyvinylpyrrolidone and magnesium aluminate metasilicate. The composition may contain inert additives, for example, lubricants such as magnesium stearate, disintegrators such as sodium carboxymethyl starch, and auxiliary dissolution agents according to general methods. If necessary, the tablets or pills may be coated with sugar coating or coated with coating agents soluble in stomach or intestine.

The liquid composition for oral administration includes, for example, pharmaceutically acceptable emulsions, liquids, suspensions, syrups and elixirs and contains inert solvents for general use, for example distilled water and ethanol. The composition may contain auxiliary agents such as solubilizers, moistening agents and suspending agents, sweeteners, flavors, aromatic agents and preservatives.

The injections for parenteral administration include sterile, aqueous or non-aqueous liquids, suspensions, and emulsions. The aqueous solvent includes, for example, distilled water for injections and physiological saline. The non-aqueous solvent includes, for example, propylene glycol, polyethylene glycol and vegetable oils such as olive oil, alcohols such as ethanol, and polysorbate 80 (product name). Such composition may additionally contain isotonic agents, preservatives, moistening agents, emulsifying agents, dispersants, stabilizers and auxiliary dissolution agents. These are sterilized by filtration through bacteria-trapping filters, blending of sterilizing agents or irradiation. Additionally, these may be used by firstly making into aseptic solid compositions and then dissolving or suspending them in sterile water or sterile solvents for injection use prior to their use.

Transmucosal agents such as inhalation agents and transnasal agents in solid, liquid or semi-solid forms are used and can be produced by the known methods. For example, excipients such as lactose and starch and pH adjusters, preservatives, surfactants, lubricants, stabilizers and thickeners may appropriately be added. For the administration, appropriate devices for inhalation or insufflation may be used. For example, using known devices, such as inhalation device for measured administration, and sprayers, the compound may be administrated singly or may be administered in a powder form of a formulated mixture or in solution or suspension in combination with pharmaceutically acceptable carriers. The inhalation devices for dry powder and the like may be devices for single administration or plural administrations. Dry powder or powder-containing capsule may be used. Otherwise, the compound may be administered in the form of appropriate sprays, such as aerosol spray under pressure, using appropriate gases such as chlorofluoroalkane, hydrofluoroalkane or carbon dioxide.

The dose is appropriately determined, depending on each case in terms of the symptom, age, sex, etc. of a subject to be administered. For the oral administration, generally, the dose is about 0.001 mg/kg to 10 mg/kg per adult per day, which is administered in one portion or two to four portions. For inhalation, the dose is within a range of 0.0001 mg/kg to 1 mg/kg per adult per administration, which is administered once or several times a day.

BEST MODE FOR CARRYING OUT THE INVENTION

Figure 1:
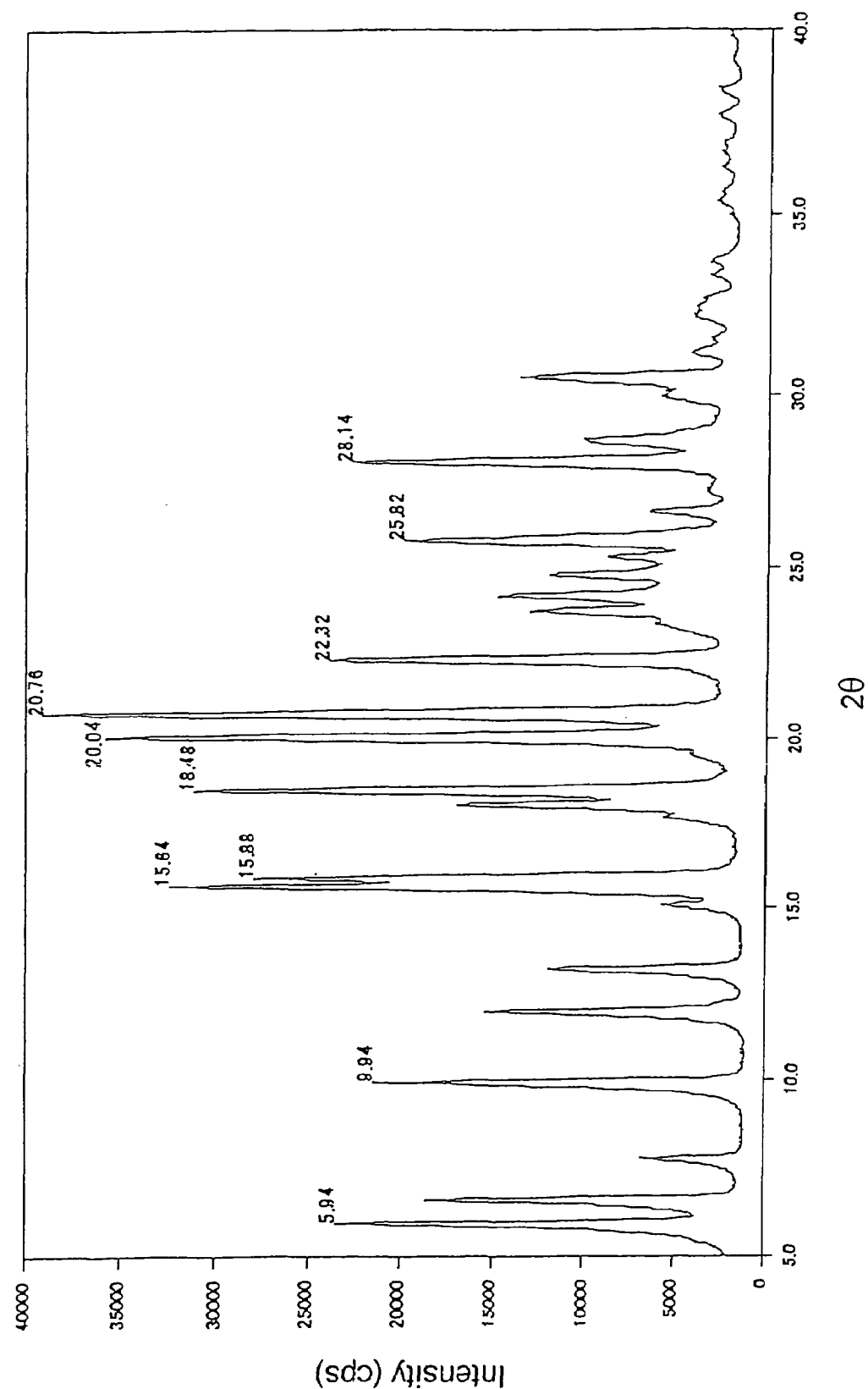
FIG. 1 X-ray powder diffraction chart of the α type crystal of 4,6-dimethyl-4'-[3,5-bis (trifluoromethyl)-1H-pyrazol-1-yl]nicotinanilide.
Figure 2:
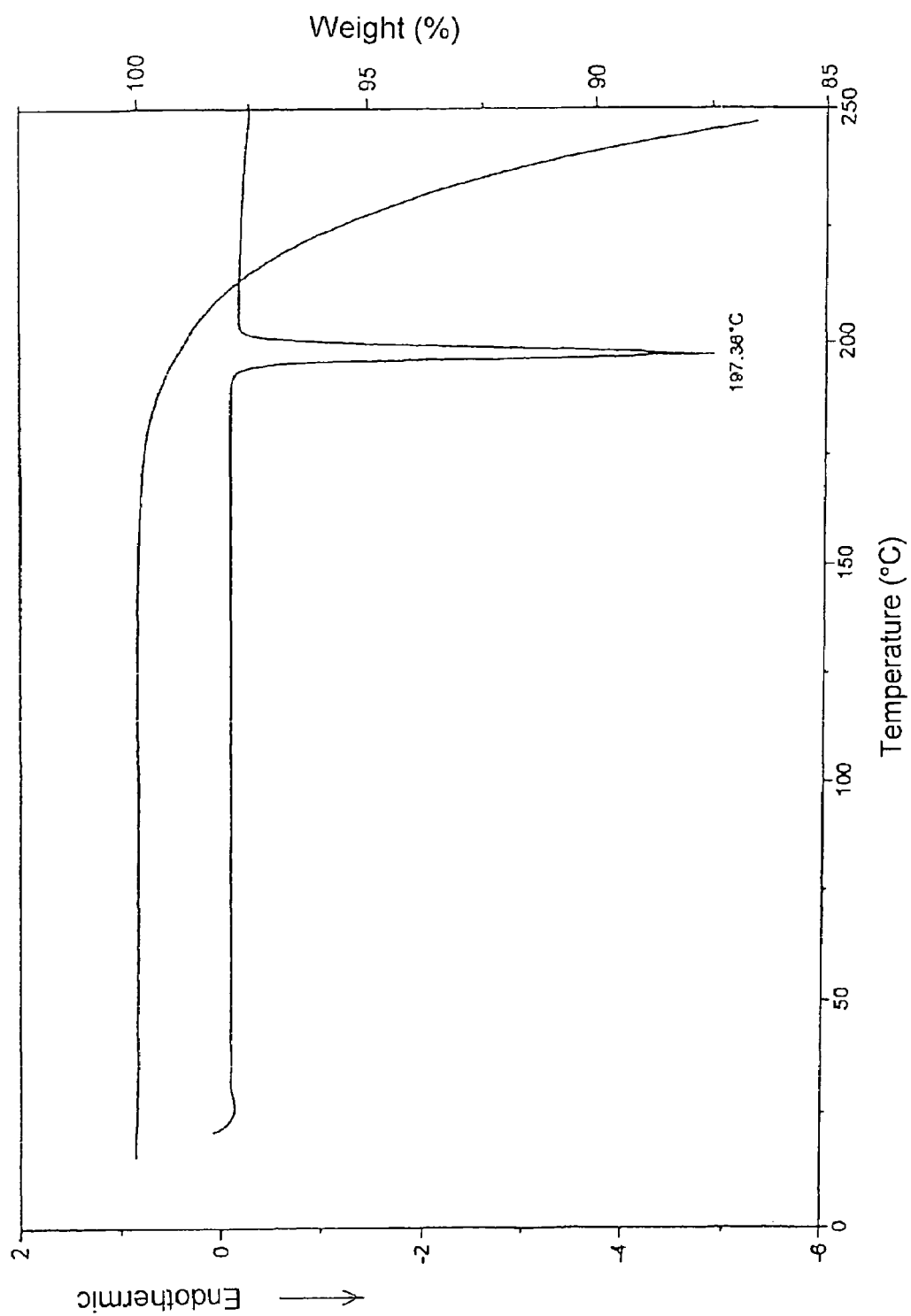
FIG. 2 Thermal analysis chart of the α type crystal of 4,6-dimethyl-4'-[3,5-bis (trifluoromethyl)-1H-pyrazol-1-yl] nicotinanilide.
Figure 3:
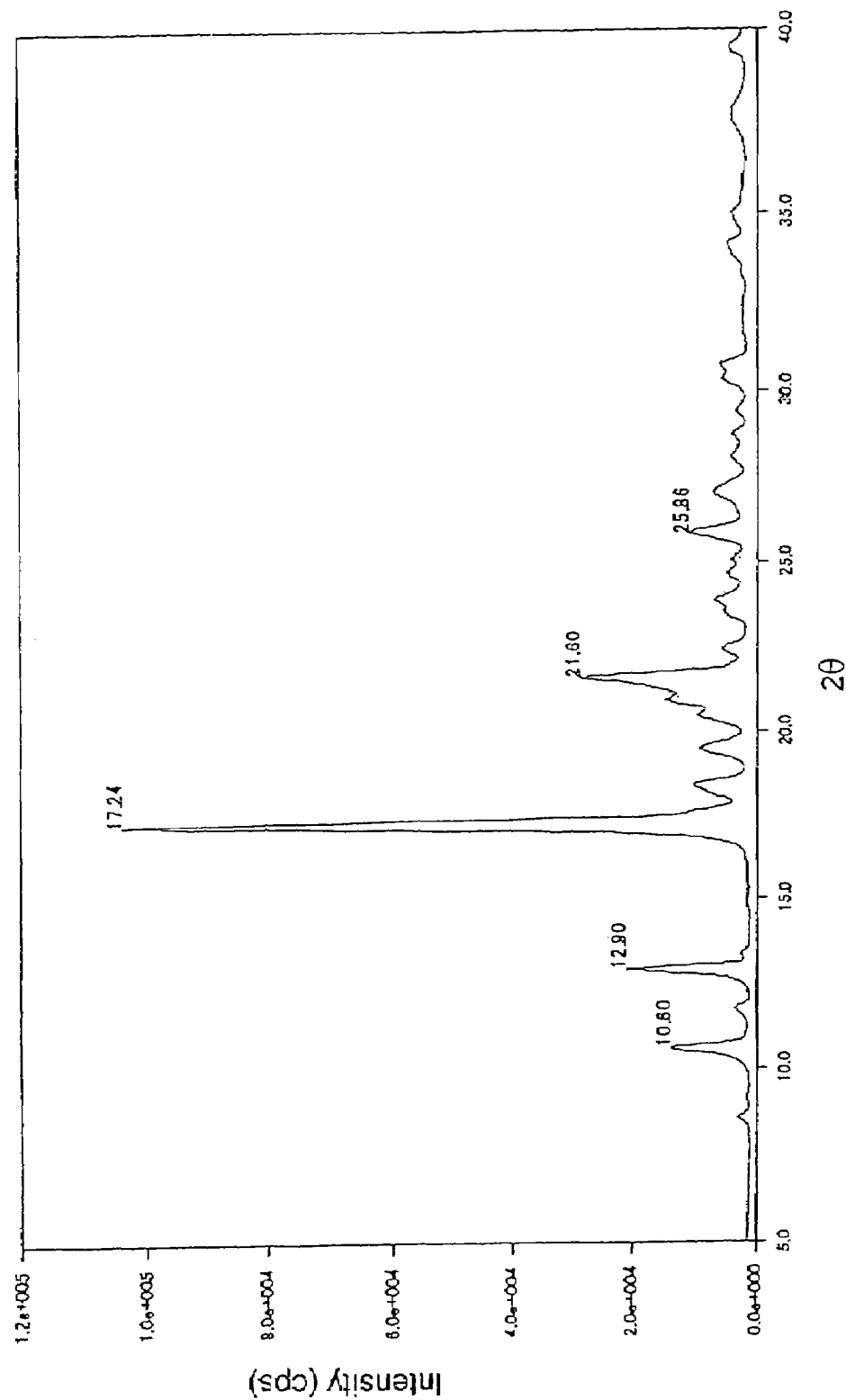
FIG. 3 X-ray powder diffraction chart of the β type crystal of 4,6-dimethyl-4'-[3,5-bis (trifluoromethyl)-1H-pyrazol-1-yl]nicotinanilide.
Figure 4:
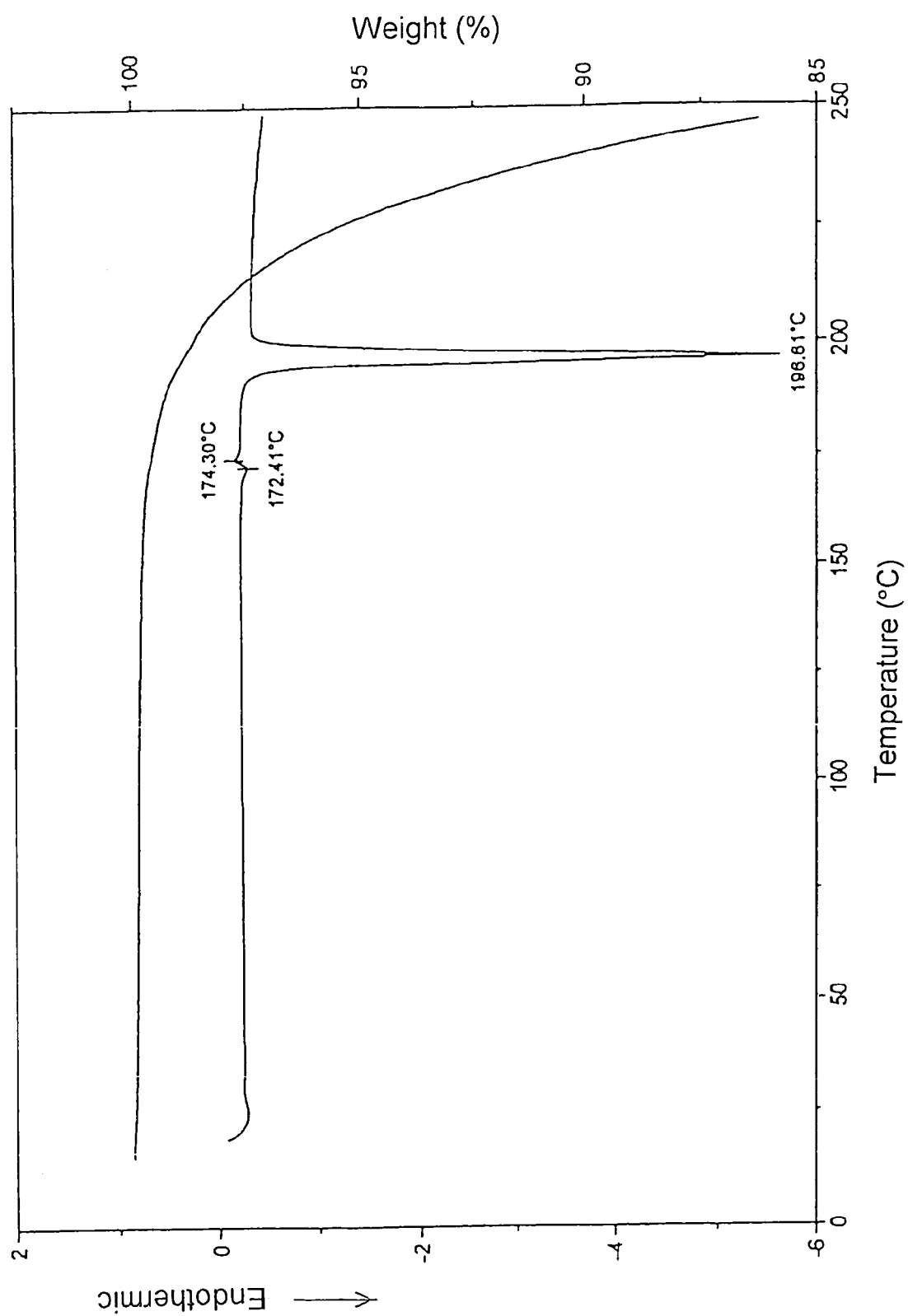
FIG. 4 Thermal analysis chart of the β type crystal of 4,6-dimethyl-4'-[3,5-bis (trifluoromethyl)-1H-pyrazol-1-yl] nicotinanilide.

The invention is now described specifically in the following Examples, which never limit the scope of the invention.

Measurement of the X-ray powder diffraction was carried out, using a sample which had been ground according to the conventional method and MXP18TAHF22 manufactured by MAC Science under the following conditions: anode: copper; tube current: 350 mA; tube voltage: 45 kV; sampling interval: 0.020°; scanning speed: 3.0°/min; wavelength: 1.54056 angstroms; scanning range (2θ): 5 to 40°.

Differential scanning calorimetry (DSC) and thermogravimetry (TG) were performed, using DSC2910 and Hi-Res TGA 2950 manufactured by TA Instruments under the following conditions: sample amount: about 5 mg; sample container: aluminium pan (open; for DSC) and platinum pan (open; for TG); heating rate: 10° C./min; temperature range for measurement: room temperature to 250° C.; atmospheric gas: dried nitrogen; and flow rate of atmospheric gas: 50 ml/min.

EXAMPLE 1

Oxalyl chloride (8.7 ml) was added to a mixture of 4,6-dimethylnicotinic acid (15.1 g) and dichloromethane (150 ml) under ice cooling, followed by stirring at 15 to 20° C. for one hour. A mixture of 4-[3,5-bis(trifluoromethyl)-1H-pyrazol-1-yl]aniline (23.59 g) and dichloromethane (300 ml) was added to the resulting reaction solution, followed by stirring at room temperature for 18 hours. An aqueous 20% potassium carbonate solution (about 200 ml) was added to the reaction solution, from which the organic layer was separated. Subsequently, the aqueous layer was extracted with dichloromethane (about 50 ml). The organic layer and the extract solution were combined together and subsequently concentrated under reduced pressure. The resulting residue was recrystallized from a mixed solvent (270 ml) of ethanol and water (2:1, respectively), to obtain 4,6-dimethyl-4'-[3,5-bis(trifluoromethyl)-1H-pyrazol-1-yl]nicotinanilide (26.70 g) as bluish white solid.

FAB-MS(Pos.): m/z 429[(M+H)$^+$]; NMR(DMSO-d$_6$) δ: 2.41 (3H, s), 2.49(3H, s), 7.24(1H, s), 7.60(2 h, d, J=8.8 Hz), 7.79 (1H, s), 7.95 (2H, d, J=8.8 Hz), 8.58 (1H, s), 10.72 (1H, s).

EXAMPLE 2

Production of the α Type Crystal

A mixture of 4,6-dimethyl-4'-[3,5-bis(trifluoromethyl)-1H-pyrazol-1-yl]nicotinanilide (8.0 g) and toluene (160 ml) was heated until the solution boiled. Subsequently, the resulting solution was stirred overnight with a spinbar, while allowing the solution to cool to room temperature. The precipitated crystal was collected by filtration, washed with toluene (10 ml) and dried overnight at 60° C. under reduced pressure, to obtain the α type crystal of 4,6-dimethyl-4'-[3,5-bis(trifluoromethyl)-1H-pyrazol-1-yl]nicotinanilide (6.52 g) as white solid.

EXAMPLE 3

Production of the β Type Crystal

2-Propanol (120 ml) was added to 4,6-dimethyl-4'-[3,5-bis(trifluoromethyl)-1H-pyrazol-1-yl]nicotinanilide (8.0 g), followed by dissolution and heating until the solution boiled. Subsequently, the resulting solution was left to stand for cooling to room temperature. No crystal precipitation was observed. Under stirring with an stirring wing, water (120 ml) was added to the solution and the mixture was stirred at room temperature for one hour and 30 minutes. The precipitated crystals were collected by filtration, washed with a mixed solvent (about 50 ml) of 2-propanol and water (1:1, respectively), and dried at 60° C. under reduced pressure for one day, to obtain the β type crystal of 4,6-dimethyl-4'-[3,5-bis(trifluoromethyl)-1H-pyrazol-1-yl]nicotinanilide (7.32 g) as white solid.

The crystals of 4,6-dimethyl-4'-[3,5-bis(trifluoromethyl)-1H-pyrazol-1-yl]nicotinanilide of the present invention, particularly the α type and β type crystals, are highly stable and useful as a raw material for producing pharmaceutical products.

The invention claimed is:

1. A crystal of 4,6-dimethyl-4'-[3,5-bis(trifluoromethyl)-1H-pyrazol-1-yl]nicotinanilide.

2. The crystal according to claim 1, which has peaks of 2θ (°) at 5.94, 9.94, 15.64, 15.88, 18.48, 20.04 and 20.76 in X-ray powder diffraction.

3. The crystal according to claim 1, which has peaks of 2θ (°) at 10.60, 12.90 and 17.24 in X-ray powder diffraction.

4. The crystal according to claim 1, which has a thermal absorption peak at 195 to 198° C. (onset) in DSC analysis.

5. The crystal according to claim 2, which has a thermal absorption peak at 195 to 198° C. (onset) in DSC analysis.

6. The crystal according to claim 3, which has a thermal absorption peak at 195 to 198° C. (onset) in DSC analysis.

* * * * *